(12) United States Patent
Luke et al.

(10) Patent No.: US 7,669,487 B2
(45) Date of Patent: Mar. 2, 2010

(54) DESORBER

(75) Inventors: John George Luke, Bristol (GB); Richard Sleeman, Bristol (GB)

(73) Assignee: Mass Spec Analytical Ltd., Bristol (GB)

( * ) Notice: Subject to any disclaimer, the term of this patent is extended or adjusted under 35 U.S.C. 154(b) by 200 days.

(21) Appl. No.: 11/100,019

(22) Filed: Apr. 5, 2005

(65) Prior Publication Data

US 2005/0217392 A1    Oct. 6, 2005

(30) Foreign Application Priority Data

Apr. 6, 2004    (EP)    ................................. 04252043

(51) Int. Cl.
   *G01N 1/22*    (2006.01)
(52) U.S. Cl. .................................. 73/863.12
(58) Field of Classification Search ............... 73/863.12
   See application file for complete search history.

(56) References Cited

U.S. PATENT DOCUMENTS

| | | | | |
|---|---|---|---|---|
| 4,046,014 A | * | 9/1977 | Boehringer et al. | ...... 73/863.12 |
| 4,732,046 A | * | 3/1988 | Lawrence et al. | ......... 73/864.21 |
| 5,123,274 A | * | 6/1992 | Carroll et al. | ............. 73/863.12 |
| 5,181,427 A | * | 1/1993 | Elias et al. | ............... 73/863.12 |
| 5,425,263 A | | 6/1995 | Davies et al. | |
| 5,476,794 A | * | 12/1995 | O'Brien et al. | ................ 436/92 |
| 5,482,524 A | * | 1/1996 | Nakano et al. | ............... 422/285 |
| 5,552,600 A | | 9/1996 | Davies et al. | |
| 5,665,314 A | * | 9/1997 | Berger et al. | ................... 422/89 |
| 5,741,984 A | | 4/1998 | Davies et al. | |
| 5,808,178 A | | 9/1998 | Rounbehler et al. | ......... 73/23.39 |
| 6,085,601 A | * | 7/2000 | Linker et al. | ............. 73/863.12 |
| 6,186,012 B1 | * | 2/2001 | Kenny et al. | ............. 73/863.12 |

FOREIGN PATENT DOCUMENTS

| | | |
|---|---|---|
| GB | 2 262 603 A | 6/1993 |
| GB | 2 363 517 A | 12/2001 |

* cited by examiner

*Primary Examiner*—Robert R Raevis
(74) *Attorney, Agent, or Firm*—Gardere Wynne Sewell LLP

(57) ABSTRACT

A desorber for use with a chemical ionisation mass spectrometer comprises a body portion that has a cavity formed therein, the cavity being arranged to receive a sample collector, the sample collector being preferably carried by a holding device that can be slid in and out of the cavity. The body portion includes an air intake passage in communication with the cavity and at least one heating element arranged to heat air drawn through the air intake passage into the cavity.

12 Claims, 4 Drawing Sheets

DESORBER

BACKGROUND TO THE INVENTION

The ability to accurately and reliably determine the presence or otherwise of a particular compound on an everyday object is of significant importance to customs and police forces around the world. The compounds of highest interest include illicit drugs and explosives and it is their detection in both a forensic context and with regard to the detection of contraband or tariff evasion that is of interest to police and customs forces respectively. Generally, the compounds of interest are likely to be present only in extremely small, or trace, amounts. Consequently, extremely sensitive chemical analysis techniques are employed to determine the presence or otherwise of a particular compound (target compound analysis).

One such analytical approach known from the prior art is to use a tandem mass spectrometer to chemically analyse a collected sample. However, the prior art techniques for analysing collected samples, and more particularly in the preparation of the samples prior to analysis by the mass spectrometer, can be both complex and time consuming. For example, bank notes would be sampled by taking bundles of bank notes and shaking them over a sheet of aluminium foil. Any particles deposited on the foil would then be vacuumed up, the vacuum cleaner including a removable filter, and the filter on the vacuum cleaner would be sampled using the tandem mass spectrometer. To sample each filter would generally require extensive sample preparation and sometimes chemical treatment prior to analysis. This would include several handling steps that would usually involve the use of solvents and the glassware. As well as being time consuming, the extensive preparation of the filters introduces an increased possibility of contamination of the sample. In addition, the sampling of bundles of money is not ideal as illicit drugs, such as cocaine, is found on most bank notes in general circulation. To determine the pattern of contamination it is necessary to analyse individual bank notes. Such individual analysis requires a large volume of individual filters to be analysed and therefore is time consuming when using prior art analysis methods. Similar problems and disadvantages are experienced when using sample collectors other than filters, such as swabs (dressings).

In UK patent application GB 2363517 A the current applicants discuss the introduction of a sample to a mass spectrometer by heating a sheet-like carrier, such as a bank note, within a confined space between two heated bodies such that a sufficient quantity of substance is desorbed from the carrier to be passed directly into the ionisation chamber of a mass spectrometer for subsequent analysis. Whilst suitable for the rapid sampling of individual bank notes, or other thin card or paper items, the apparatus described in GB 2363517 A is not suitable for use with filters or other sample collectors, of the type referred to above. This is because the sampled particles contained in such sample collectors tend, in addition to collecting on the surface, to be embedded in the collector material, as opposed to simply being present on the surface of a bank note. It should also be understood that the filters are used to remotely collect samples (by adsorbtion) where it is not possible to directly desorb the artefact of interest, such as a banknote. Direct desorption of an artefact, such as a banknote, is the most desirable method because it is the most efficient. Most sample collectors (adsorbers) are at best only a few percent efficient. This being so, a very effective desorption method is necessary to transfer the collected material into the instrument ionization region. Also materials of interest are most efficiently desorbed from the filter when subjected to their optimum desorption temperature, this temperature varies according to the material of interest.

GB-A-2 262 203 discloses a desorbing unit for analysis of vapours and particles desorbed from a porous flexible sampling disc. The unit includes two metal blocks that define a cavity therebetween in which the sampling disc is placed. The blocks incorporate straight air passages that allow air to pass through the sampling disc under pressure. The blocks are maintained at a high temperature. U.S. Pat. No. 5,741,984 describes an apparatus for the collection of a chemical sample from the fingers of an individual for subsequently analysis comprising a token that is removed from a dispenser. A token handler for use in association with the token and an analyzer is also disclosed.

SUMMARY OF THE INVENTION

According to an embodiment of the present invention there is provided a desorber comprising a body portion having a cavity formed therein arranged to receive a sample collector, the body portion including an air intake passage in communication with the cavity and at least one heating element, characterised in that the air intake passage is labyrinthine in form and the at least one heating element is in close proximity to a portion of the air intake passage, such that in use air drawn through the air intake passage is raised to substantially the same temperature as the at least one heating element.

Additionally or alternatively, the body portion may further include an air outlet passage in communication with the cavity. Additionally the air intake passage and air outlet passage may be arranged such that, in use, air is drawn through a sample collector located in the cavity from the air intake passage and is exhausted out of the air outlet passage.

The desorber may further include a sample collector holding device arranged to support a sample collector and to be removably received in the cavity.

BRIEF DESCRIPTION OF THE DRAWINGS

Embodiments as described herein are disclosed by means of illustrative example, with reference to the accompanying figures, of which.

DESCRIPTION OF PREFERRED EMBODIMENTS OF THE INVENTION

Figure 1:
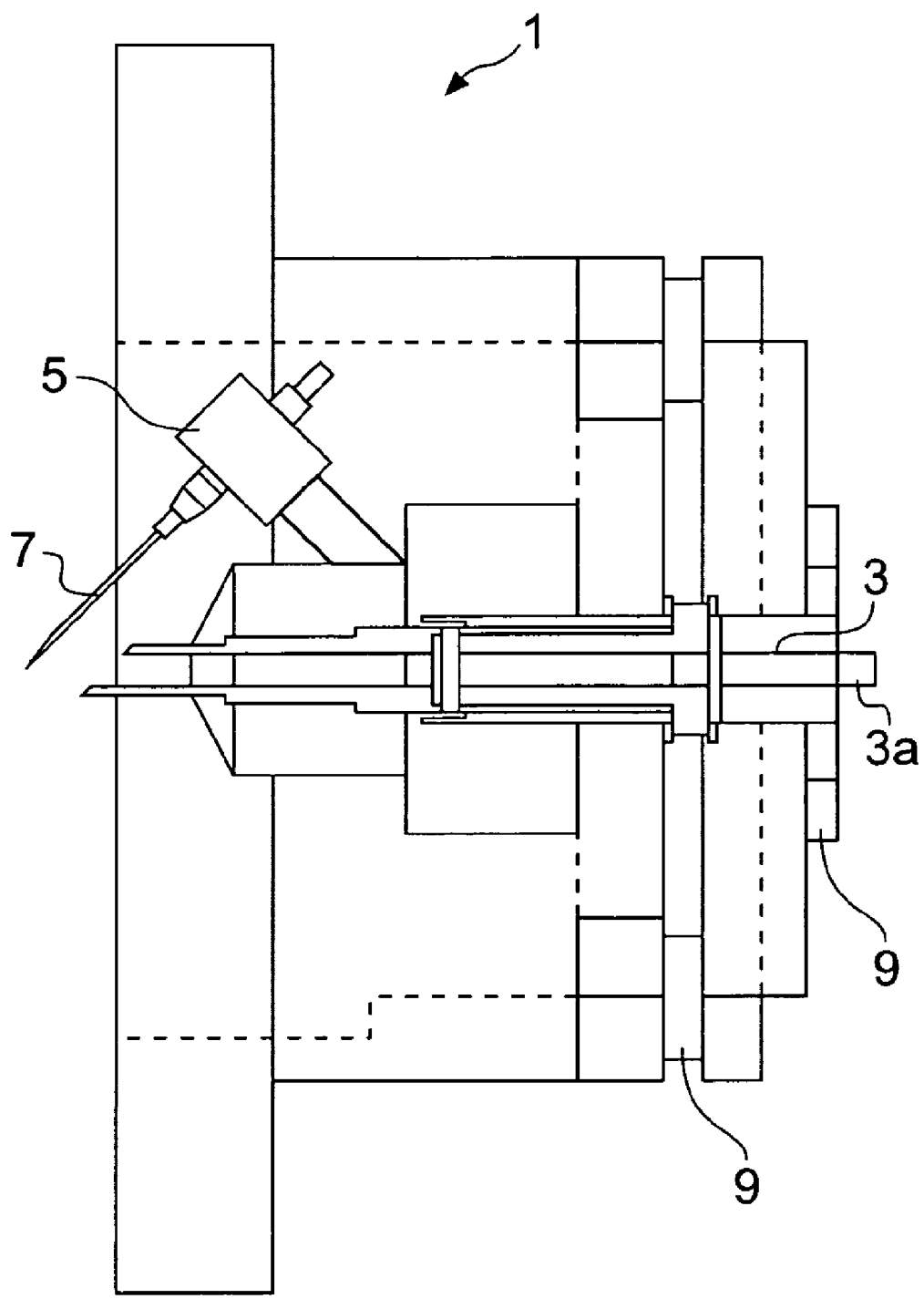
FIG. 1 illustrates in cross section the sample input portion of a mass spectrometer analysis device as described herein.

FIG. 1 illustrates in general cross section an input interface assembly that allows a desorber according to embodiments of the present invention to be connected to a tandem mass spectrometer. The interface assembly 1 includes a brass transfer line 3 that in use transfers the desorbed sample from the sample collector to plenum chamber of the mass spectrometer. Also shown is the ioniser needle assembly 5 that comprises a high voltage electrode 7 (e.g. at 8 kV). The corona discharge of the high voltage electrode 7 causes immediate ionisation of any substances entering the main chamber for analysis in a known manner. Other ionisation techniques may also be used. A number of ceramic insulators 9 are provided to thermally insulate the interface assembly 1 and the mass spectrometer itself (not shown) from the high temperatures present in the desorber apparatus.

Figure 2:
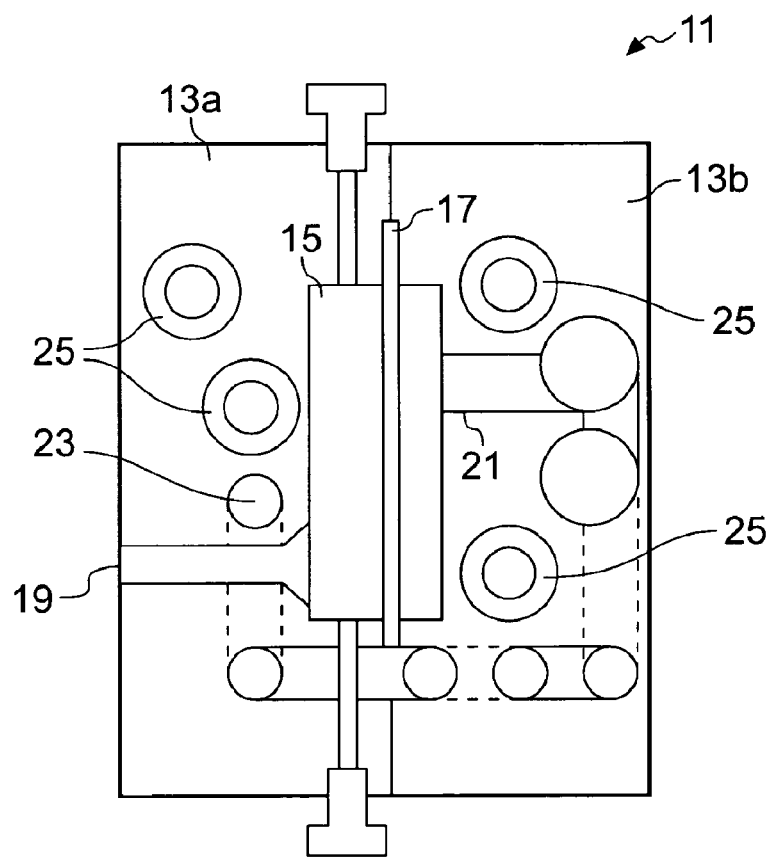
FIG. 2 schematically illustrates in cross section a desorber according to an embodiment as described herein.
Figure 3:
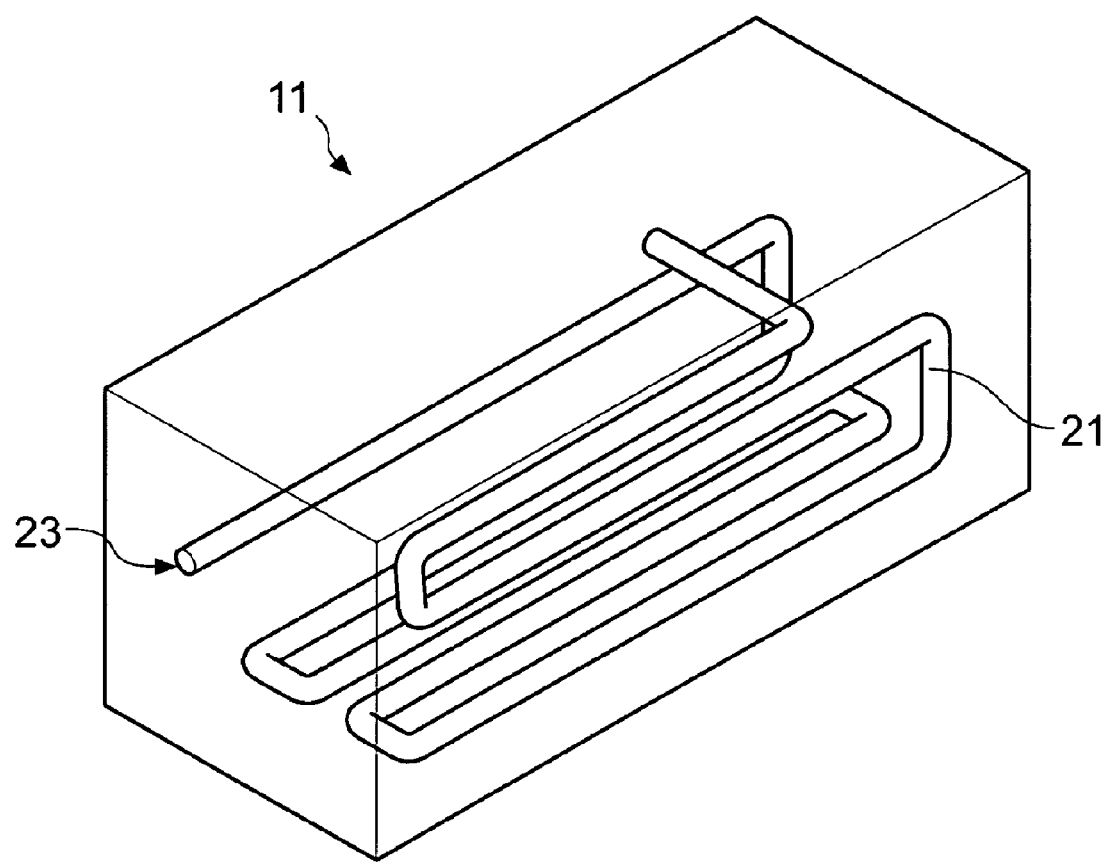
FIG. 3 schematically illustrates in perspective view the air flow passageway of the Desorber shown in FIG. 3.
Figure 5:
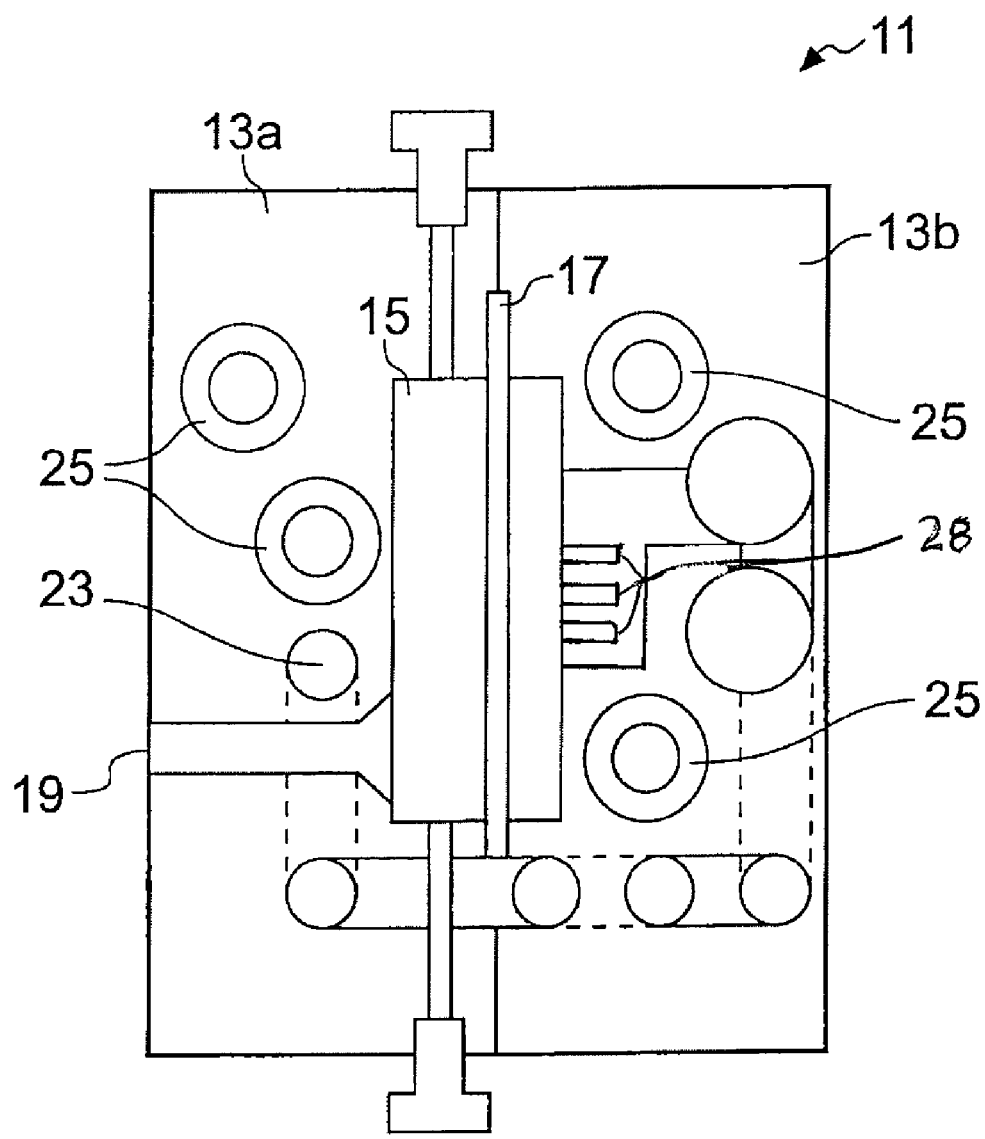
FIG. 5 schematically illustrates in cross section a desorber according to another embodiment As described herein.

FIG. 2 schematically illustrates a cross sectional view of a desorber according to an embodiment of the present invention. The desorber 11 comprises first and second desorber blocks 13a, 13b that are securely fastened to one another by any suitable means (not shown), for example by a number of threaded screws. Each of the desorber blocks 13a and 13b has on its respective mating surface a substantially rectangular recess formed therein, such that the two recesses form a substantially rectangular cavity 15 when the two desorber blocks are secured to one another. The recesses in the desorber blocks are also shaped so as to define an input slot 17 that extends from one end of the cavity 15 to the outer surface of the desorber 11 and provides an input passage for introducing a sample collector into the cavity 15 of the desorber 11. In the first desorber block 13a a substantially cylindrical passage 19 is formed in communication with the cavity 15 and the exterior of the desorber. When the desorber 11 is secured to the input interface 1 shown in FIG. 1, the exterior orifice of the passage 19 is aligned with an end 3a of the brass transfer line 3 of the interface, thus providing an input passage for the flow of desorbed material from the cavity of the desorber 11 through the passage 19 and the transfer line 3 to the analysis chamber of the mass spectrometer. A second passage 21 is formed in the second desorber block 13b and is also in communication with the cavity of the desorber. It will be noted that when a sample collector, such as a filter, is in place in the desorber unit 11, the sample collector substantially bisects the cavity 15, with the first and second passages 19, 21 opening onto the cavity 15 on either side. The passage 21 extends through the second desorber block 13b in a labyrinthine fashion and is continued through to the first desorber block 13a in which it exits the desorber 11 at an orifice 23. The term "labyrinthine" is used in this context to refer to a passageway that purposefully does not follow either the most direct or convenient route and which preferably follows a route that causes the passageway to turn back on itself one or more times. Consequently a labyrinthine passageway in this context has a total length considerably in excess of that necessary simply to provide a connection between any two given points. The labyrinthine nature of the second passageway 21 is illustrated schematically in FIG. 3. Referring back to FIG. 2, a number of electrical resistance cartridge heaters 25 are embedded in each of the desorber blocks 13a, 13b, which are preferably of a good heat conductive material, for example aluminium.

Figure 4:
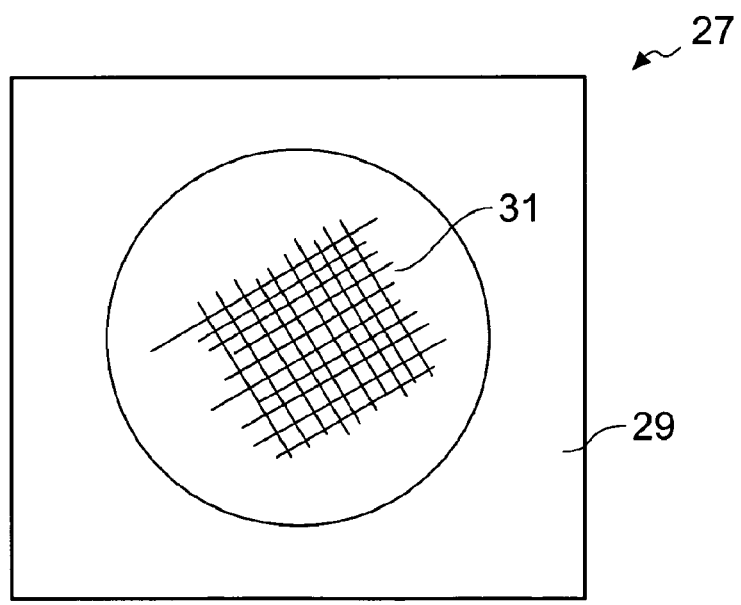
FIG. 4 illustrates a sample collector for use with a desorber as described herein.

In use, a sample collector on which a product sample has been gathered is inserted into the slot 17 in the desorber 11. The sample collector is preferably held by an appropriate holding device to allow the easy withdrawal of the sample collector from the desorber. However, in other embodiments of the present invention the sample collector may be placed directly into the slot 17, or may be conveyed through the desorber by means of a sample transport mechanism comprising, for example, of one or more pairs of driven rollers that grip the sample collector, or a driven endless belt on which the sample collector may be placed and conveyed through the desorber. It will be appreciated that in such embodiments the slot 17 would preferably extend completely through the desorber and would preferably be horizontal. An illustrative example of a sample collector 27 is shown in FIG. 4 and comprises a substantially rectangular or square card filter holder 29 having a large aperture formed therein, the aperture being covered by a filter material 31. The filter material may be, amongst other materials, an adsorbent paper, a fine ceramic mesh or a finely woven cloth.

The sample collector 27 and the corresponding holding device are suitably dimensioned such that they preferably bisect the cavity 15 formed within the desorber unit 11. The desorber unit 11 is attached to the interface assembly 1 that is in turn attached to the main body of the mass spectrometer.

Air is drawn through the transfer line 3 of the interface assembly and therefore through the first and second passageways 19, 21 of the desorber unit 11. The air drawn into the transfer line of the mass spectrometer is therefore drawn through the sample collector 27. The cartridge heaters 25 heat the two desorber blocks 13a and 13b, which in turn heats the air within the cavity 15 of the desorber unit 11. The cartridge heaters 25 are arranged to be in relatively close proximity to a significant proportion of the labyrinthine passage 21. This therefore allows the air that is drawn into the labyrinthine passage 21 via the aperture 23 to be raised to substantially the same temperature as the cartridge heaters 25 and the body of the desorber blocks 13a and 13b. As a consequence, the hot air that is drawn through the sample collector 27 is at a sufficiently high temperature to cause any volatile substances that are generally indicative of the presence of illicit or explosive substances to be desorbed and transferred via the passageway 19 to the mass spectrometer for subsequent analysis. The cavity filter receiving slot is preferably closely related in width to the thickness of the filter holder such that through the labyrinth rather than through the filter receiving slot, thus ensuring that stable high temperature air is draw through the filter.

In alternative embodiments arranged for desorbing relatively large sample collectors, such as items of cloth or clothing, without the use of a sample collector holder there may be a number of openings formed in the block 13b in communication with the cavity 15. A proposed arrangement is that a manifold is formed in the block 13b that comprises a number of further passageways 28 each in communication with the second passageway 21 and in communication with the cavity 15. In this manner the heated air from the second passageway 21 can be drawn through the sample collector in a number of locations, thus improving desorption of the sample.

Only by providing a labyrinthine passage 21 of sufficient length does the air drawn through the passage attain a sufficiently high temperature for reliable desorption of the filter sample to occur. The placement of the cartridge heaters is also a factor in heating the entrained air to a sufficient degree. Additionally, drawing the heated air through the sample collector, as opposed to merely placing it within a heated cavity, provides particular advantages and improvements in the desorption process such that a particularly reliable and efficient desorption process occurs. The desorber unit of the present invention both greatly increases the speed of processing and greatly reduces the handling and preparation stages required.

The invention claimed is:

1. A desorber comprising a body having:
   an open cavity formed within the body and having first and second opposing sides and being arranged to removably receive a sample collector between said opposing sides;
   a first air passage formed integrally within the body and opening onto the first side of the open cavity;
   a second air passage formed integrally within the body and opening onto the second side of the open cavity, the second air passage being labyrinthine in form; and
   one or more heating elements together being in close proximity to a majority of the second air passage and arranged to raise the temperature of a majority of the second air passage such that air drawn through the second air passage is heated to substantially the same temperature as the one or more heating elements prior to the heated air being drawn through the open cavity.

2. The desorber according to claim 1 further comprising a sample collector holding device arranged to support a sample collector and to be removably received in the cavity.

3. The desorber according to claim 1, wherein the body includes a plurality of heating elements.

4. The desorber according to claim 1, wherein the second air passage terminates at an orifice open to the atmosphere.

5. The desorber according to claim 1, wherein the body comprises a plurality of further air passages each in communication with the open cavity and in communication with the second air passage.

6. The desorber according to claim 1, wherein the body comprises one or more metallic blocks.

7. The desorber according to claim 1, wherein the one or more heating elements heat the body which in turn heats the majority of the second air passage.

8. The desorber according to claim 1, wherein the one or more heating elements are in close proximity to a portion of the first air passage.

9. A desorber comprising a body having:
   an open cavity formed within the body and having first and second opposing sides and being arranged to removably receive a sample collector between said opposing sides;
   a first air intake passage formed integrally within the body and opening onto the first side of the open cavity;
   a second air passage formed integrally within the body and opening onto the second side of the open cavity, the second air passage being labyrinthine in form; and
   at least one heating element in close proximity to a portion of the second air passage and arranged to raise the temperature of air drawn through the second air passage to substantially the same temperature as the at least one heating element prior to the heated air being drawn through the open cavity, wherein the second air passage terminates at an orifice open to the atmosphere.

10. The desorber according to claim 9 further comprising a sample collector holding device arranged to support a sample collector and to be removably received in the cavity.

11. The desorber according to claim 9, wherein the body includes one or more further air passages each in communication with the open cavity and in communication with the second air passage.

12. The desorber according to claim 9, wherein the body comprises one or more blocks portions securely fastened to one another.

* * * * *